United States Patent [19]

Ham et al.

[11] 4,093,615
[45] June 6, 1978

[54] CYCLIC OLIGOMERS OF N-SUBSTITUTED AZIRIDINES

[75] Inventors: George E. Ham, Lake Jackson; Ruben L. Krause, Angleton, both of Tex.

[73] Assignee: The Dow Chemical Company, Midland, Mich.

[21] Appl. No.: 435,049

[22] Filed: Jan. 21, 1974

Related U.S. Application Data

[63] Continuation of Ser. No. 180,236, Sep. 13, 1971, abandoned.

[51] Int. Cl.$^2$ .................. C07D 255/02; C07D 257/02; C07D 259/00
[52] U.S. Cl. .......................... 260/239 BC; 260/239 E
[58] Field of Search ...................... 260/239 BC, 239 E

[56] References Cited

U.S. PATENT DOCUMENTS 3,458,818  12/1969  Thompson .................... 260/239 BC

OTHER PUBLICATIONS

Tsuboyama et al., Tetrahedron Letters No. 16, pp. 1367–1370 (1970).
Hansen et al., J. Het. Chem., vol. 5, p. 305 (1968).
Dermer et al., Ethylenimine and Other Aziridines, (Academic Press, 1969), pp. 317–322 and 327–332.

Primary Examiner—Donald G. Daus
Assistant Examiner—D. B. Springer
Attorney, Agent, or Firm—L. Wayne White; David H. Fifield

[57] ABSTRACT

Novel cyclic oligomers of the formula

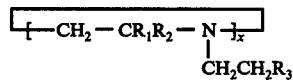

are prepared by contacting (a) a strong protic acid with (b) an N-substituted non-activated aziridine of the formula

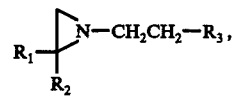

wherein $R_1$ and $R_2$ are independently hydrogen or lower alkyl and $R_3$ is hydrogen, hydroxyl, cyano or an organic radical which is inert in the process. The process is typically conducted in an aqueous alkanol medium. E.g. the cyclic tetramer of N-phenethylaziridine was obtained as the predominant product by heating a solution of N-phenethylaziridine in aqueous ethanol at reflux temperatures in the presence of p-toluenesulfonic acid.

11 Claims, No Drawings

CYCLIC OLIGOMERS OF N-SUBSTITUTED AZIRIDINES

CROSS-REFERENCE TO RELATED APPLICATIONS

This application is a continuation of our earlier copending application Ser. No. 180,236 filed Sept. 13, 1971, now abandoned.

BACKGROUND OF THE INVENTION

The synthesis of 1,4,7,10-tetrabenzyl-1,4,7,10-tetraazocyclododecane,

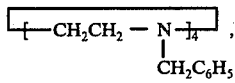

was reported by G. R. Hansen and T. E. Burg, J. Heterocyclic Chem. 5 (2), 305 (1968). Their synthesis comprises refluxing a mixture of N-benzylaziridine and p-toluenesulfonic acid in aqueous ethanol. The authors reported this as being an isolated reaction since they were not successful in synthesizing cyclic oligomers from other aziridines.

S. Tsuboyama et al. in *Tetrahedron Letters*, No. 16, 1367 (1970), reported the synthesis of 1,4,7,10-tetrabenzyl-2,5,8,10-tetra-(R)-ethyl-1,4,7,10-tetraazocyclododecane in about 30 percent yield from N-benzyl-2-ethylaziridine using BF$_3$.etherate as the catalyst.

SUMMARY OF THE INVENTION

Novel cyclic oligomers have been discovered which are represented by the general formula

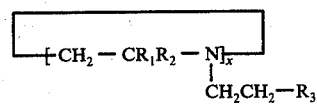

wherein (a) $x$ is an integer of from 3 to about 8, (b) $R_1$ and $R_2$ are independently hydrogen or lower alkyl (such as methyl, ethyl, propyl, butyl and the like); and (c) $R_3$ is hydrogen, hydroxyl, cyano, or an organic radical which is inert during the process of preparing the oligomers. The novel cyclic oligomers, hereafter "cyclomers", are generally high boiling liquids or solids at ambient temperatures and are soluble in many conventional organic solvents.

The cyclomers are generally obtained as homologous mixtures with the predominant species being the cyclic trimer, tetramer, and pentamer, with the tetramer being the most predominant.

The cyclomers have tertiary amine groups in their rings which can enter into many conventional reactions for tertiary amines, e.g., quaternization. Thus, the cyclomers are useful in neutralizing up to 1 equivalent of acid per amine group; in stabilizing chlorinated solvents (e.g. CH$_3$CCl$_3$) against degradation by acid; removing acidic gases, e.g. SO$_2$, from gas streams; as epoxy curing agents; as urethane catalysts; etc.

In stabilizing chlorinated solvents, the cyclomers are used in amounts of up to about 5 weight percent, based on weight of chlorinated solvent.

In curing epoxy resins, the cyclomers may be used in amounts up to about 1 amine equivalent per epoxy equivalent although smaller quantities are typically satisfactory, such as from about 0.1 up to about 0.5 amine equivalent per epoxy equivalent.

Obviously, the cyclomers may be used individually or as mixtures in the above utilities.

The novel cyclomers are conveniently prepared by contacting in an aqueous alkanol solution (a) an aziridine of the formula

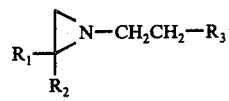

wherein $R_1$–$R_3$ have the aforesaid meaning with (b) a small but catalytic amount of a strong protic acid, such as HCl, H$_2$SO$_4$, H$_3$PO$_4$, p-toluenesulfonic acid, etc. The alkanol medium is typically an alkanol of from 1 to 4 carbon atoms, or mixtures thereof. Aqueous ethanol is the currently preferred medium. The amount of acid catalyst used may vary to convenience. However, amounts of acid up to about 5 weight percent, based on aziridine monomer, have been used with satisfactory results. Satisfactory reaction rates are generally obtained at temperatures of from about 75° C. to about 150° C. The cyclomers can be isolated and recovered by conventional techniques, such as distillation, gel permeation chromatography, etc. Gel permeation chromotography is particularly convenient and is thus preferred for recovering the higher molecular weight species.

The aziridinyl reactants here used are N-substituted, non-activated (basic) aziridines and are represented by Formula (II). They are a known class of compounds having known methods of preparation, as illustrated in "Ethylenimine and Other Aziridines", by O. C. Dermer and G. E. Ham, Academic Press, N.Y. (1969).

Illustrative of the novel cyclic oligomers are the cyclic trimer, tetramer, pentamers, etc. produced by using in the aforementioned process the aziridinyl reactants of Formula (II) wherein $R_1$ and $R_2$ are each hydrogen and $R_3$ in hydrogen; hydroxyl; cyano; hydrocarbyl of from 1 to about 24 carbon atoms, such as alkyl (e.g. methyl, butyl, decyl, hexadecyl, etc.), aryl (e.g., phenyl, naphthyl, etc.), alkaryl (e.g., tolyl, xylyl, 4-t-amylphenyl, etc.), aralkyl (e.g., benzyl, phenethyl, etc.), alkenyl (e.g. vinyl, allyl, etc.), and the like; and the corresponding hydroxy-substituted hydrocarbyl radicals (e.g. hydroxyethyl, p-hydroxyphenyl, etc.); or $R_3$ is the corresponding hydrocarbyl radicals joined by an ester

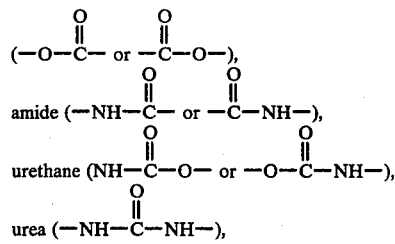

or ether (—O—) linkage. Those aziridinyl reactants having $R_3$ joined via an ester, amide, urethane, urea or ether linkage are generally prepared by reacting (A) the appropriate acid (or lower alkyl ester thereof), isocyanate or hydrocarbyl halide (e.g. chloride) with (B) one of the following aziridines $$R_1 \underset{R_2}{\triangleleft} N-CH_2CH_2-OH \quad\quad R_1 \underset{R_2}{\triangleleft} N-CH_2CH_2-NH_2$$

(III)                           (IV)

under conventional process conditions (as illustrated in "Ethylenimine and Other Aziridines"). Alternatively, those aziridinyl reactants having $R_3$ joined via an ester or amide linkage may be prepared by reacting (A) the appropriate alcohol or amine with (B)

$$R_1 \underset{R_2}{\triangleleft} N-CH_2CH_2-\overset{O}{\underset{\|}{C}}-OH \quad (V)$$

(or lower alkyl ester thereof). $R_1$ and $R_2$ have the aforesaid meanings in each instance.

The preferred species in (I) and (II) are those wherein $R_1$ is hydrogen and $R_2$ is hydrogen, methyl or ethyl (preferably hydrogen) and $R_3$ is hydrogen, hydroxy, alkyl of from 1 to about 10 carbon atoms, phenyl or $$-O-\overset{O}{\underset{\|}{C}}-R_4,$$

wherein $R_4$ is an alkyl group of from about 8 to about 24 carbon atoms (preferably from about 16 to about 20 carbon atoms and most preferably is a linear alkyl group of 17 carbon atoms); and $x$ is 3, 4 or 5.

The following examples further illustrate the invention. The molecular weights reported in the following examples were all determined by gpc (gel permeation chromatography) and were within experimental error of calculated values.

EXAMPLE 1

Cyclomers of N-Phenethylaziridine

A mixture of N-phenethylaziridine (10.0 g.) and p-toluenesulfonic acid (0.05 g.) in 75 ml of 95% aqueous ethanol was refluxed (83° C.) for 25 hours. The solvent and volatiles were removed from the resulting mixture under reduced pressure (30° C. at 1 mm. Hg. and briefly at 50° C.) leaving a liquid residue (8.5 g.). The residue was approximately 50 weight percent unreacted N-phenethylaziridine; as determined by vapor phase chromatography (vpc). The residue was separated into its components by using gel permeation chromatography (gpc) techniques to give: (A) 1.10 g. of the cyclic tetramer having characteristic infrared (ir) absorption bands at 990 cm.$^{-1}$ and 1300 cm.$^{-1}$ and a molecular weight (m.w.) of 570, and (B) 0.12 g. of the cyclic pentamer having an average molecular weight of 850. The ir and nuclear magnetic resonance (nmr) spectra of (A) and (B) were consistent with the assigned cyclic structure and free of any absorption attributable to end groups. These cyclomers were miscible in essentially all proportions in ethanol, acetone, benzene, tetrahydrofuran and carbon tetrachloride.

EXAMPLE 2

Cyclomers of N-Ethylaziridine

The procedure of Example 1 was repeated using N-ethylaziridine (14.5 g.) and p-toluenesulfonic acid (0.15 g.) in 240 ml. of 95% aqueous ethanol. The cyclic tetramer (m.w. 268), pentamer (m.w. 345) and hexamer (m.w. 465) were isolated and identified as above. The cyclic tetramer had characteristic ir absorption bands at 975 cm.$^{-1}$ and 1300 cm.$^{311}$. The highest mass to charge ratio (m/e) in the mass spectra of the cyclic tetramer was 284 (calc. 284). The cyclomers were likewise miscible in essentially all proportions in ethanol, acetone, benzene, tetrahydrofuran and carbon tetrachloride.

EXAMPLE 3

Cyclomers of N-Ethylaziridine

N-ethylaziridine (5.66 g.) and p-toluenesulfonic acid (0.25 g.) in approximately 80 ml. of 95% aqueous ethanol were heated in a sealed autoclave for 2 hours at 125° C. The mixture was analyzed by vpc, from which it was determined that 2.55 g. of the N-ethylaziridine was converted. The cyclic tetramer (1.50 g.) was separated from the mixture by distillation under reduced pressure; b.p. 110–120° C. at 0.5 mm. Hg. The cyclic trimer was likewise separated from the mixture; b.p. 50–60° C. at 0.5 mm. Hg. Higher cyclomers were obtained but were not isolated by distillation.

EXAMPLE 4

Cyclomers of N-(2-Hydroxyethyl)Aziridine

The procedure of Example 1 was repeated using N-(2-hydroxyethyl)aziridine (11.8 g.) and p-toluenesulfonic acid (0.10 g.) in 158 ml. of 95% aqueous ethanol. The mixture was refluxed for 12 hours. The cyclic trimer (m.w. 260) and tetramer (m.w. 378) and a mixture of higher cyclomers were separated from the reaction mixture. The cyclic tetramer had a characteristic ir absorption at 1000 cm.$^{-1}$ and 1300 cm.$^{-1}$. Highest m/e in the mass spectra for the cyclic tetramer was 348 (calc. 348).

EXAMPLE 5

Cyclomers of N-n-Decylaziridine

The procedure of Example 1 was repeated using N-n-decylaziridine (12.63 g.) and p-toluenesulfonic acid (0.05 g.) in 72 ml. of 95% aqueous ethanol. The mixture was refluxed for 18 hours. The cyclic tetramer (m.w. 680), pentamer (m.w. 835) and hexamer (m.w. 1200) were isolated by gpc techniques as the predominant products. The tetramer had a characteristic ir absorption at 980 cm.$^{-1}$ and 1305 cm.$^{-1}$.

EXAMPLE 6

Cyclomers of N-[2-(Ethoxycarbonylamino)Ethyl]-Aziridine

The procedure of Example 1 was repeated using $$\triangleleft N-CH_2CH_2-NH-C(O)-O-C_2H_5$$

(10.9 g.) and p-toluenesulfonic acid (0.05 g.) in 75 ml. of 95% aqueous ethanol. The cyclic trimer (m.w. 505), tetramer (m.w. 720) and a mixture of higher cyclomers were isolated from the reaction mixture by gpc techniques.

EXAMPLE 7

Cyclomers of N-(2-Stearoyloxyethyl)Aziridine

Concentrated HCl (0.15 ml.) was added to a rapidly stirred mixture of

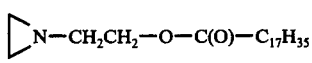

(10 g.) and water (90 g.). The resulting mixture, which had the appearance of an emulsion, was heated at reflux temperature for 1 hour. The water was then removed under reduced pressure and the crude product resolved by gpc techniques. The cyclic tetramer (m.w. 1350) was obtained as the predominant product. It had characteristic ir absorption bands at 980 cm.$^{-1}$ and 1305 cm.$^{-1}$.

In each of the above examples, the products had ir and nmr spectra consistent with the assigned cyclic structure and the spectra were free of absorptions attributable to end groups.

The products from Examples 1–7 are useful bases and may be used to neutralize up to 1 equivalent of HCl (or other acid) per amine equivalent and are useful stabilizers in chlorinated solvents (e.g. $CH_3Cl_3$) to inhibit or prevent acid (e.g. HCl) degradation of the solvent. Amounts of up to about 5 weight percent are typical.

Further, the products are useful as epoxy curing agents. The amount used may vary to obtain a particular hardness in the final product or to obtain a particular rate of cure. Typically, however, the curing agents are mixed with an epoxy resin (such as the diglycidyl ether of bisphenol-A) in amounts of from 0.1 to about 0.5 amine equivalent per epoxy equivalent and the mixture warmed (e.g. at about 100° C.) until cured. The utility of the cyclomers in this area is enhanced by their solubility in various common organic solvents.

Other cyclomers described in the text of the disclosure are similarly prepared and used.

We claim:

1. A cyclic oligomer of the formula

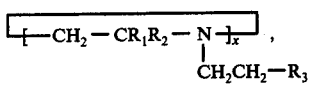

wherein
 (a) $x$ is an integer of from 3 to 8;
 (b) $R_1$ and $R_2$ are independently hydrogen or lower alkyl; and
 (c) $R_3$ is hydrogen, hydroxyl, cyano, a hydrocarbyl radical $R_4$ selected from the group consisting of alkyl, aryl, alkaryl, aralkyl and alkenyl, the corresponding hydroxy-substituted $R_4$ hydrocarbyl radical or $R_3$ is represented by one of the formulas

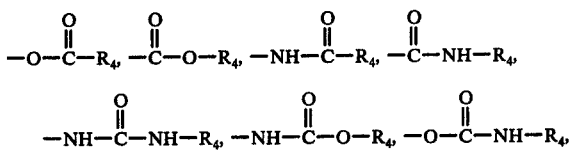

and $-O-R_4$, wherein each hydrocarbyl radical $R_4$ has from 1 to 24 carbon atoms.

2. The cyclic oligomer defined in claim 1 wherein $R_1$ is hydrogen and $R_2$ is hydrogen, methyl or ethyl.

3. The cyclic oligomer defined in claim 2 wherein $R_2$ is hydrogen.

4. The cyclic oligomer defined in claim 1 wherein $R_3$ is hydrogen, hydroxyl, alkyl of from 1 to 10 carbon atoms, phenyl or

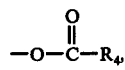

wherein $R_4$ is an alkyl group of from 8 to 24 carbon atoms.

5. The cyclic oligomer defined in claim 4 wherein $R_4$ is an alkyl group of from 16 to 20 carbon atoms.

6. The cyclic oligomer defined in claim 1 wherein $x$ is 3, 4 or 5.

7. The cyclic oligomer defined in claim 3 wherein $R_3$ is hydrogen, hydroxyl, octyl, phenyl, $-NH-C(O)-C_2H_5$ or $-O-C(O)-C_{17}H_{35}$.

8. The cyclic oligomer defined by claim 3 wherein $R_3$ is hydrogen or alkyl of from 1 to 10 carbon atoms.

9. The cyclic oligomer defined by claim 3 wherein $R_3$ is phenyl.

10. The cyclic oligomer defined by claim 3 wherein $R_3$ is

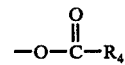

and wherein $R_4$ is an alkyl group of from 16 to 20 carbon atoms.

11. The cyclic oligomer defined in claim 10 wherein $R_4$ is a linear alkyl group of 17 carbon atoms.

* * * * *